United States Patent [19]

Espinosa et al.

[11] Patent Number: 5,452,232
[45] Date of Patent: Sep. 19, 1995

[54] METHOD AND APPARATUS FOR DETERMINING A PROPERTY OR YIELD OF A HYDROCARBON PRODUCT BASED ON NIRA OF THE FEEDSTOCK

[75] Inventors: Alain Espinosa; Didier C. Lambert, both of Lavera; Andre Martens, Chateauneuf les Martigues; Gilbert Ventron, Lavera, all of France

[73] Assignee: BP Oil International Limited, London, England

[21] Appl. No.: 357,047

[22] Filed: Dec. 13, 1994

Related U.S. Application Data

[63] Continuation of Ser. No. 252,973, Jun. 1, 1994, abandoned, which is a continuation of Ser. No. 954,702, Sep. 30, 1992, abandoned, which is a continuation of Ser. No. 549,660, Jul. 9, 1990, abandoned, which is a continuation of Ser. No. 233,190, Aug. 17, 1988, abandoned.

[30] Foreign Application Priority Data

| Aug. 18, 1987 | [FR] | France | 87 11678 |
| Aug. 18, 1987 | [FR] | France | 87 11680 |
| Aug. 18, 1987 | [FR] | France | 87 11681 |
| Aug. 18, 1987 | [FR] | France | 87 11682 |
| Aug. 18, 1987 | [FR] | France | 87 11683 |
| Aug. 18, 1987 | [FR] | France | 87 11684 |
| Aug. 18, 1987 | [FR] | France | 87 11685 |
| Aug. 18, 1987 | [FR] | France | 87 11686 |
| Jul. 12, 1988 | [FR] | France | 88 09492 |

[51] Int. Cl.$^6$ .......................... G06F 15/46; G01J 3/42
[52] U.S. Cl. ..................... 364/498; 364/499; 364/502; 356/326; 208/DIG. 1; 250/339.08; 250/339.09; 250/339.12
[58] Field of Search .............. 364/502, 497, 498, 499; 324/307, 310, 312; 356/300, 303, 326; 382/17; 250/226, 339.08, 339.09, 339.12; 208/113, 157

[56] References Cited

U.S. PATENT DOCUMENTS

| 2,926,253 | 2/1960 | Munday | 250/435 |
| 3,121,677 | 2/1964 | Coggeshall et al. | 208/178 |
| 3,666,932 | 5/1972 | White | 235/151.12 |
| 3,693,071 | 9/1972 | Dolbear | 324/0.5 R |
| 3,896,312 | 7/1975 | Brown et al. | 250/343 |
| 4,236,076 | 11/1980 | Judge et al. | 250/347 |
| 4,251,870 | 2/1981 | Jaffe | 364/500 |
| 4,267,572 | 5/1981 | Witfe | 364/498 |
| 4,286,327 | 8/1981 | Rosenthal et al. | 364/498 |
| 4,318,616 | 3/1982 | Chamran et al. | 364/498 |
| 4,323,309 | 4/1982 | Akitomo et al. | 364/498 |
| 4,357,668 | 11/1982 | Schwartz et al. | 364/497 |
| 4,397,958 | 8/1983 | Vroom | 364/497 |
| 4,568,186 | 2/1986 | Yoshimura et al. | 364/498 |
| 4,642,778 | 2/1987 | Hieftje | 364/498 |

(List continued on next page.)

FOREIGN PATENT DOCUMENTS

1465253 1/1966 France.
2545938 11/1984 France.

OTHER PUBLICATIONS

"Process Analytical Chemistry", Callis et al. Analytical Chemistry, vol. 59, No. 9, pp. 624A–637A, May 1, 1987.
"Near Infrared Spectroscopy of Organic Substances", Weyer, 594 Applied Spectroscopy Reviews 21, No. 1&2, pp. 1–43, 1985.

(List continued on next page.)

Primary Examiner—Michael Zanelli
Attorney, Agent, or Firm—Brooks Haidt Haffner & Delahunty

[57] ABSTRACT

The properties and yield of a product from a hydrocarbon conversion or separation process may be determined from the NIR (Near Infrared) spectrum of the feedstock. This is accomplished by: (a) determining with an IR spectrometer the absorbance of the feedstock at a certain number of frequencies in the spectral range 16667 to 3840 cm$^{-1}$ starting from a defined base line, and then (b) determining the property or yield by applying a correlation between the property or yield and the absorbance values. The correlation is determined experimentally by multivariate regression and is dependent upon the type of spectrometer employed, the property or yield to be determined, and the frequencies used.

22 Claims, 1 Drawing Sheet

U.S. PATENT DOCUMENTS

| | | | |
|---|---|---|---|
| 4,660,151 | 4/1987 | Chipman et al. | 364/498 |
| 4,701,838 | 10/1987 | Swinkels et al. | 364/164 |
| 4,766,551 | 8/1988 | Begley | 364/498 |
| 4,800,279 | 1/1989 | Hieftje et al. | 250/339 |
| 5,023,804 | 6/1991 | Hoult | 364/497 X |
| 5,046,846 | 9/1991 | Ray et al. | 364/498 A |
| 5,082,985 | 1/1992 | Crouzet et al. | 585/501 |

OTHER PUBLICATIONS

Avery et al., "Infra-red Spectra of Hydrocarbons. II Analysis of Octane Mixtures by the Use of Infra-red Spectra obtained at Low Temperatures", J. Applied Physics, vol. 18, Nov. 1947, pp. 960-967.

Healy et al., "A New Approach to Blending Octanes", API Division of Refining, 24th mid-year meeting (New York City, Division of Refining 27 May 1959, vol. 39 III, 1959, 132-192).

Buchanan et al., "Trends in Near infra-red Analysis", Trends in Analytical Chemistry, vol. 5, No. 6, 1986, pp. 154-157.

Article: "Near-Infra red Reflectance Spectrometry: Tip of the Iceberg", Analytical Chemistry, vol. 56, No. 8, Jul. 1984.

Article: "New Method may Determine Octane Ratings of Gasoline Quicker, Better", Hydrocarbon Processing, Jul. 1987, p. 19.

Hibbard et al., "Carbon-Hydrogen Groups in Hydrocarbons", Analytical Chemistry, vol. 21, No. 4, pp. 486-492 (Apr. 1949).

Stark et al., "Near-Infrared Analysis (NIRA): A Technology for Quantitative and Qualitative Analysis", Applied Spectroscopy Reviews, 22(4), pp. 335-339 (1986).

Honigs, D. E., "Near-Infrared Analysis", Analytical Instrumentation, 14(1), 1-62 (1985).

Schoen et al., "Calculating Gasoline Blend Octane Ratings", Industrial and Engineering Chemistry, vol. 49, No. 9, pp. 1740-1742, Sep. (1985).

Gary et al., Petroleum Refining, 2nd edition, Marcel Dekker, New York, 1984.

Myers et al., "Determination of Gasoline Octane Numbers from Chemical Composition" Analytical Chemistry, vol. 47, No. 13, pp. 2301-2304, Nov. 1975.

Honigs et al., "Near-Infrared Determination of Several Physical Porperties of Hydrocarbons", Analytical Chemistry, vol. 57, No. 2, Feb. 1985, pp. 443-445.

Whetsel, K. B. "Near Infrared Spectrophotometry". Applied Spectroscopy Reviews, 2(1), (1-67) (1968).

Honigs et al., "Near-Infrared Reflectance Analysis by Gauss-Jordan Linear Algebra", Applied Spectroscopy, vol. 37, No. 6, 1983, pp. 491-497.

Borisevich et al., "Instrumentation and Automation Equipment Method for Determining Group Hydrocarbon Composition and the Octane Number of Reforming Gasolines with IR Spectroscopy for Purposes of Operation Control"; Avtomatizatsiya 1981; No. 3 pp. 13-15.

Dornheim et al., "Optimum Non-Linear Gasoline Blending", The Oil and Gas Journal, May 26, 1958.

Kelly et al., Analytical Chemistry, (1989), 61, 313-320, "Prediction of Gasoline Octane Numbers etc.".

Jones et al., Chemical Engineering, Oct. 9, 1978, pp. 111-114, "Near Infrared Analyzers Refine Process Control".

Jones, Instrument Society Bulletin No. 0-87644-687-9, (1982), pp. 21-25 "Near-Infrared Analysis In The Process Industry".

Murrill, Instrument Society of America, (1981), pp. 12-15 "Fundamental of Process Control Theory".

Callis, Abstract submitted for Lecture, Aug. 8, 1986.

Illman et al., Abstract submitted for Workshop, Sep. 1, 1986.

Callis, Lecture Notice, Sep. 22, 1986.

Callis, Abstract submitted for Lecture, Sep. 24, 1986.

Callis, Abstract for Lecture, Nov. 5-7, 1986.

Callis, Abstract for Paper in Analytical Chemistry; undated.

METHOD AND APPARATUS FOR DETERMINING A PROPERTY OR YIELD OF A HYDROCARBON PRODUCT BASED ON NIRA OF THE FEEDSTOCK

REFERENCE TO RELATED APPLICATIONS

This application is a continuation, of application Ser. No. 08/252,973, filed Jun. 1, 1994, now abandoned, which is a continuation, of application Ser. No. 07/954,702, filed Sep. 30, 1992, now abandoned, which is a continuation of application Ser. No. 07/549,660 filed Jul. 9, 1990, now abandoned, which was a continuation of application Ser. No. 7/233,190 filed Aug. 17, 1988, now abandoned.

This invention relates to a method for the determination of the properties of the feedstock, the properties of the product and/or the yield of the product in a hydrocarbon conversion or separation process by carrying out NIR (near infra red) spectroscopic analyses of the feedstock and correlating these with the desired properties. The method is suitable for use on-line and in real time and for incorporation in process control.

Callis et al, Analytical Chemistry, Vol 59, No. 9, pp 624A–636A (May 1987) mentions the possibility of determining the octane rating of an unleaded gasoline by NIR spectroscopy and point out in this particular case, the existence of a connection between other properties of the products and the NIR spectra of the products.

However, when a product is produced by converting or separating various components, which are often themselves mixtures, major problems are encountered in predicting the properties of the final products. This arises from the fact that several properties do not follow linear laws.

For certain processes, models exist which enable the prediction of products and yields. To use these, however, it is usually necessary to know the properties of the feed in detail, the chemical composition, the molecular weights of the components etc. This information is normally obtained by laboratory analyses which involves a delay in obtaining the results.

According to the present invention there is provided a method for the determination of the properties of the product and/or the yield of the product in a hydrocarbon conversion or separation process wherein the method comprises the following steps:

(a) determining with an IR spectrometer the absorbance of the feedstock at a certain number of frequencies in the spectral range 16667 to 3840 cm$^{-1}$ (0.6 to 2.6 microns), preferably 12500 to 3840 cm$^{-1}$ (0.8 to 2.6 micron), most preferably 4760 to 4000 cm$^{-1}$ (2.1 to 2.5 micron) starting from a defined base line, and (b) determining the property by applying a correlation between the property and the absorbance values, the correlation being determined experimentally by multivariate regression, depending on the type of spectrometer used, the property required, and the frequencies used.

The frequencies used may be selected from the following:
4670 cm$^{-1}$
4640
4615
4585
4485
4405
4390
4385
4332
4305
4260
4210
4170
4135
4100
4070
4060
4040

The corresponding frequencies expressed in statutory units (Hz) are obtained by multiplying these values by $3 \times 10^{10}$, the velocity of light in cm/s.

This choice is neither exhaustive nor exclusive. The choice of other frequencies will not alter the method but will require the use of other coefficients in the models enabling the calculation of the desired properties sought from the spectra.

The base line (regarded as corresponding to zero absorbance) is preferably 4780 cm$^{-1}$.

BRIEF DESCRIPTION OF THE DRAWINGS

The FIGURE is a block diagram of a process and analytical instrumentation for implementing the invention.

DETAILED DESCRIPTION OF THE INVENTION

Figure 1:
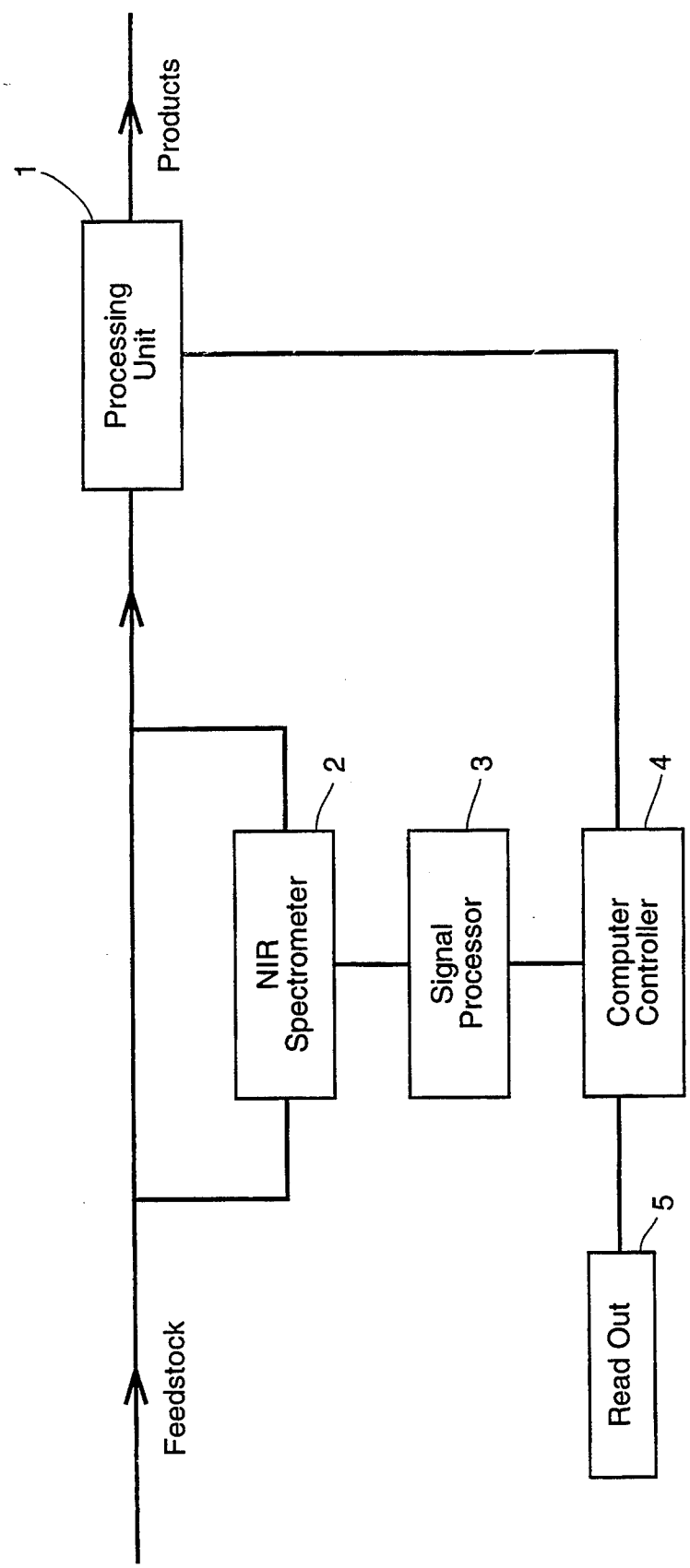

The processing equipment 1 may be computer controlled by a feed-back control system for altering process conditions in response to variations in the property and/or yield of the product from the desired value, from the determination of the NIR spectrum of the feedstock.

The spectrometer 2 may be linked to a signal processing device 3 to permit numerical treatment of the spectrum, preferably by Fourier transformation.

The spectrometer suitably has a resolution power of 4 cm$^{-1}$.

The method may be used on-line and in real time.

The correlation may contain linear terms, quadratic terms and homographic (ratio) terms.

According to a specific embodiment, the hydrocarbon conversion process may be a catalytic reforming process and the properties may be selected from the following: yields of gasoline ($C_5^+$), hydrogen and gas, octane numbers (clear or leaded), vapor pressure and density.

The correlation in this case may be either linear for a feed of relatively constant composition, for example the KUOP characteristic varying between 11.8 and 12.2 (terms p of equation (1) below), or can involve quadratic terms (terms q of equation (1)) or homographic (ratio) terms (terms r of equation (1)) for a feed of varying composition, the KUOP characteristic varying between 10.8 and 12.2.

The KUOP characteristic or Watson factor is expressed by the formula:

$$\sqrt{\frac{\text{boiling point (Rankine scale)}}{\text{density 60/60}}}$$

Rankine scale = absolute Fahrenheit scale
Density 60/60 = density of the product at 60° F. compared to water at 60° F.

$$X = C + \Sigma p_i \cdot D_i + \Sigma q_{ij} D_i D_j + \Sigma r_{ij} D_i/D_j \qquad (1)$$

$D_i \ldots D_j$ are absorbances at the wavelengths in question.

The constant C and the various coefficients p, q and r are obtained from multivariate digital analysis techniques applied to a set of feedstocks used for preliminary calibration.

In the computer-assisted operation of a reformer, the NIR spectrum of the feed as it enters the unit is taken in real time and is treated as an information vector which continuously monitors the potential of the feed.

The abundance of the NIR spectrum and the experimental accuracy obtained, resulting from the accumulation of spectral data by fast Fourier transformation, means that this information is both accurate and relevant to the chemical operations involved in the reforming process. The NIR spectrum is therefore a numerical indicator of the suitability of the feed for reforming.

Furthermore, it has been observed that the differential spectrum, when measured in real time, constitutes a digital signal enabling computer assisted operation of the unit to be improved. Catalytic reforming results in an increase in octane number which is related to the severity of the operating conditions for a given state of activity of the catalyst.

It has been noted that the differential spectrum can be directly correlated with the gain in octane number (motor and/or research) of the clear or leaded product at different levels of tetraethyl or tetramethyl lead and is related to the severity of the process.

It is therefore possible to have a sensitive and accurate method of computer assisted control for a catalytic reformer by continuously monitoring the differential spectrum, enabling parameters to be adjusted to produce gasoline of the specified octane number, regardless of variation in the quality of the feed.

With this new method of operating the unit, variations in the differential spectrum in the NIR sensitively and rapidly optimise processing conditions using a computer programme.

Thus, according to a modification of the above embodiment, the hydrocarbon conversion process may be a catalytic reforming process wherein the method comprises the further steps of:

(c) carrying out differential spectrum measurements in the same range and at the same frequencies on the feedstock and the product, (d) applying a correlation between the differential spectrum and the octane number gain, the correlation being determined experimentally by multivariate regression analysis, (e) comparing the sum of the two values thus determined (octane number and octane number gain) with a desired objective, and (f) modifying the operating conditions of the catalytic reformer until the determined octane number gain is in agreement with the desired octane number gain.

In catalytic reforming the frequencies used may be selected from the following:
4670 cm$^{-1}$
4485
4332
4305
4210
4100
4060
4040

The correlation between the differential spectrum and the octane number gain may be a linear correlation, e.g.

$$\text{Octane gain} = aO + \sum_{i=1}^{7} ai\, DD_i \qquad (2)$$

where $aO$ and $ai$ are constants and $DD_i$ is the input/output differential spectrum for wavelength i.

According to another embodiment, the hydrocarbon conversion process may be a selective hydrogenation process and the property may be the maleic anhydride number of the product.

The feedstock may be a $C_5$-200° C. fraction derived from steam cracking called steam cracked gasoline.

The process is not restricted to this type of product, however, similar gasolines being derived from other types of cracking reaction.

It is possible to determine on-line and in real time the level of diolefins in steam cracked gasoline selectively hydrogenated, starting with the NIR spectrum of the steam cracked gasoline as it enters the unit. This is done under given operating conditions and for a catalyst of defined composition and activity.

The process based on the invention is not restricted to this particular property, however, it is possible to predict other properties of the product, for example:
  the content of olefins
  the clear octane numbers and those for leaded gasolines, different levels of tetraethyl lead or tetramethyl lead Analysis by spectrometer in the NIR range makes it possible to calculate by differing numerical methods several properties of a hydrocarbon fraction from its spectrum.

According to a further embodiment, the hydrocarbon conversion process may be a catalytic hydrocracking process and the properties may be selected from the following: total conversion of the feedstock to product and conversion to gasoline.

In this case, the frequencies used are preferably selected from the following:
4585 cm$^{-1}$
4390
4332
4260
4210
4170
4100
4070

The sum of the absorbances for the eight wavelengths considered is reduced to 100 and thereafter the relative percentage of absorption for a given band will be used. Hence, if $D_i$ is the absorbance for the wavelength i, then:

$$\sum_{i=1}^{8} D_i = S \qquad (3)$$

and the percentage of relative absorption for the frequency i: $p_i$ will be equal to:

$$p_i = \frac{D_i}{S} \times 100 \qquad (4)$$

The feedstock may be vacuum distillates, atmospheric residues, extracts derived from lube oil processing, hydrogenated residues, deasphalted residues, cracked distillates and cat cracker recycle oils.

According to yet another embodiment, the hydrocarbon conversion process may be a catalytic cracking process and the properties are selected from the following:

(i) the conversion of the feed to gasoline and the yield of residue in the product,
(ii) the density, research octane number (RON) and motor octane number (MON) of clear and leaded gasolines from the cracking process.

For catalytic cracking, the frequencies may be selected from the following:

4670 cm$^{-1}$
4615
4485
4135
4100
4060

The feed may be a distillate, for example, vacuum distillate gas oils, an atmospheric residue (deasphalted or not), a lube oil extract, a hydrogenated or deasphalted residue, a cracked distillate or a cat cracker recycle oil.

Some of the properties which may be determined include:

the research octane number (RON) and the motor octane number (MON) of the gasoline produced, whether clear or leaded, and at different levels of lead,
the cetane number of gas oil,
the densities of various fractions produced (gasoline, gas oil, residue),
the viscosity of the residue, etc.

By combination with computer control of a fluidised bed catalytic cracker, the NIR spectrum allows complete and accurate characterisation of the feed which, together with the processing conditions of the unit (for example, inlet and outlet temperature of the heater, C/O (ratio of the catalyst flow rate to the feed flow rate), space velocity, nature and activity of the catalyst, etc) leads to an efficient, computer model.

It is thus possible to control the unit with great precision.

According to another embodiment, the hydrocarbon conversion process may be a visbreaking process and the properties may be selected from the following: the yield of the gas oil product, the viscosity, specific gravity and xylene equivalent of the residue, and the conversion limit, i.e, the maximum conversion before an unstable residue is produced.

The feedstock may be atmospheric or vacuum distillate residues. They may be used in a blend and may have various petroleum fractions added to them: e.g. lube oil extracts, hydrogenated or deasphalted residues, cracked distillate units, catalytic cracker recycled oils, etc.

In addition to the hydrocarbon conversion processes exemplified above, the method is also applicable to the control of separation processes such as distillation.

Thus according to another embodiment, the hydrocarbon separation process may be a distillation process and the properties may be selected from the following:

(i) the quantitative composition of a mixture of crude oils constituting the feedstock when the distill and is known to be a blend of crude oils,
(ii) the yields of products obtained,
(iii) the densities and viscosities of the various products,
(iv) the cetane number, aniline point, cloud point and the KUOP characterisation factor of the gas oil,
(v) the n-paraffinic, isoparaffinic, cycloparaffinic and aromatic content of the gasoline and the research octane number (RON) and motor octane number (MON) of clear and leaded gasoline with different contents of tetraethyl or tetramethyl lead.

In computer assisted operation of a processing unit, the NIR spectrum of the feedstock entering the unit is thus taken in real time and treated as an information vector which characterises the processing properties of the feedstock in the process on a continuous basis. The detail in the NIR spectrum and the experimental precision which may be obtained from the accumulation of spectral data ensures that this information is reliable and relevant to processing operations.

The analysis and data processing time is less than 1 minute.

According to another aspect of the present invention there is provided apparatus for carrying out a method for the determination of the properties of the product and/or the yield of the product in a hydrocarbon conversion or separation process as hereinbefore described, the apparatus comprising an infrared spectrometer linked to a computer programmed in such manner that the property may be determined continuously and in real time.

The apparatus may comprise a feedback control system for computer control 4 of the processing equipment in response to variations of the property and/or yield of the product from the desired value, from the determination of the NIR spectrum of the feedstock.

On-line analysis may use fibre optics as a means for transmitting light signals or may involve physical transferance of a sample to the cell of the spectrometer.

The invention is illustrated but not limited with reference to the following examples:

EXAMPLE 1

Catalytic Reforming

Operating conditions of the reformer were as follows:
reactor temperature: 510° C.
LHSV: 1.85
catalyst: $R_{12}$ UOP
pressure: 39 bar The NIR spectrum of the feed at the entry to the reformer was determined at four frequencies, $F_1$, $F_2$, $F_3$ and $F_4$.

The product yield and RON of the product were then predicted using the following equations (5) and (6):

$$\text{RON clear} = 2151.36 \, D_5 + 131.22 \, D_{14} + 280.67 \, D_9 - 243.157 \qquad (5)$$

$$\text{Yield } C_5^+ = -114.84 \, D_{14} + 227.18 \, D_{16} + 338.81 \, D_9 - 249.3 \text{ \% vol} \qquad (6)$$

$D_i$ represents the absorbance of the NIR spectrum at frequency $F_i$, the zero base being taken as 4780 cm$^{-1}$.

The predictions were then compared with the actual results obtained by conventional means.

The feedstock was a highly paraffinic naphtha having a KUOP factor of 12.2, a 90% ASTM distillation point of 135° C. and a density $d^{15}$ of 0.686.

NIR spectrum:

| Frequency | | Absorbance | |
| --- | --- | --- | --- |
| $F_1$ | 4485 cm$^{-1}$ | $D_1$ | 0.0347 |
| $F_2$ | 4100 | $D_2$ | 0.55594 |
| $F_3$ | 4060 | $D_3$ | 0.61466 |
| $F_4$ | 4305 | $D_4$ | 0.65502 |

| | Yield % vol | RON Clear |
| --- | --- | --- |
| Predicted properties from equations (5) and (6) | 81.2 | 88.3 |
| Actual properties by experiment | 80.4 | 88.0 |

EXAMPLE 2

Catalytic Reforming

Example 1 was repeated using a diferent feedstock.

This was a moderately paraffinic naphtha having a KUOP factor of 11.8, a 90% ASTM distillation point of 148° C., and a density d$^{15}$ of 0.7421.

Absorbance values at the same frequencies as Example 1 were:

| | |
| --- | --- |
| $D_1$ | 0.0364 |
| $D_2$ | 0.52127 |
| $D_3$ | 0.60595 |
| $D_4$ | 0.66828 |

| | Yield % vol | RON Clear |
| --- | --- | --- |
| Predicted properties from equations (5) and (6) | 88.3 | 91.1 |
| Actual properties by experiment | 87.6 | 91.4 |

EXAMPLE 3

Catalytic Reforming (1) The octane number of the naphtha feedstock to the reformer was obtained from its NIR spectrum at the following frequencies:

| Frequency | | Absorbance | |
| --- | --- | --- | --- |
| $F_1$ | 4670 cm$^{-1}$ | $D_1$ | 0.01223 |
| $F_2$ | 4485 | $D_2$ | 0.03878 |
| $F_3$ | 4332 | $D_3$ | 0.9339 |
| $F_4$ | 4100 | $D_4$ | 0.6167 |
| $F_5$ | 4040 | $D_5$ | 0.6083 |
| $F_6$ | 4305 | $D_6$ | 0.6794 |
| $F_7$ | 4210 | $D_7$ | 0.4800 |

The research octane number values were obtained after adding 0.4 g/l tetraethyl lead.

Operating conditions of the reformer were as follows:
reactor temperature 510° C.
LHSV 1.85
catalyst $R_{12}$ UOP
pressure 39 bar As before, the octane number ON of the product from the feed is predicted by equation (1) in the form:

$$ON = C + \Sigma\, p_i D_i + \Sigma\, q_{ij} D_i D_j + \Sigma\, r_{ij} D_i / d_j$$

The constant C and the various coefficients p,q and r are obtained from multivariate digital analysis techniques applied to a set of feedstocks used for preliminary calibration.

Equation (1) becomes:

$$(RON - 0.4) = -65.52 - 3.178\, D_4.D_6 + 180.3\, D_2 - 6.32\, D_3 - 1814\, D_5.D_6 + 1232.D_5 + 1165.D_6 - 109\, D_7$$

The RON calculated by means of Equation (1) is 83.2 compared with an experimental value of 83.5.

A similar procedure could be followed for other clear or leaded octane numbers.

(2) The octane gain is estimated by Equation (2):

$$\text{Octane gain} = \alpha O + \sum_{i=1}^{7} \alpha i D \cdot D_i$$

where $\alpha O$ and $\alpha i$ are constants and D $D_i$ is the input-/output differential spectrum for the frequency i.

The values of the constants are as follows:
$\alpha O = 25.32$
$\alpha 1 = 136.48$
$\alpha 2 = -268.14$
$\alpha 3 = 51.15$
$\alpha 4 = 138.756$
$\alpha 5 = -68.40$
$\alpha 6 = 61.85$
$\alpha 7 = -288.12$ The absorbance of the NIR spectrum of the feedstock and product were as follows for the frequencies investigated:

Under these conditions Equation (2) gives an octane increase of 13.5.

(3) In view of the quality of the feedstock and the product specification an octane increase of 15 is required.

Consequently the reforming temperature must be progressively increased until the required gain is achieved. This operation is carried out by increasing the temperature by 4° C.

In this operation the differential spectrum serves as a guide in increasing the temperature. This type of adjustment based on the differential spectrum remains valid even if the nature of the feedstock changes during adjustment of the temperature.

EXAMPLE 4

Selective Hydrogenation

The operating conditions of a gasoline selective hydrogenation unit were as follows:
temperature entering the reactor: 70° C.
temperature emerging from the reactor: 170° C.
through-put of hydrogen: 45 Nm$^3$/m$^3$ of batch
V.V.h = 4
total pressure: 15 bars
palladium catalyst: Procatalyse LD 265.

The unit was fed with a steam cracked gasoline having a maleic anhydride number of 40.2. The hydrogenated gasoline has a maleic anhydride number of 7.

| Frequencies cm$^{-1}$ | | Spectrum of Feedstock Absorbance | Spectrum at Outlet from reactor Absorbance |
| --- | --- | --- | --- |
| 4670 | $D_1$ | 0.18186 | 0.18476 |
| 4615 | $D_2$ | 0.14555 | 0.14888 |
| 4585 | $D_3$ | 0.16501 | 0.17428 |
| 4485 | $D_4$ | 0.11747 | 0.07242 |
| 4332 | $D_5$ | 0.56587 | 0.58186 |
| 4260 | $D_6$ | 0.46701 | 0.4934 |
| 4170 | $D_7$ | 0.29995 | 0.30184 |
| 4100 | $D_8$ | 0.35576 | 0.34264 |
| 4060 | $D_9$ | 0.95571 | 0.98812 |
| 4040 | $D_{10}$ | 0.50597 | 0.50567 |

-continued

| Frequencies cm$^{-1}$ | | Spectrum of Feedstock Absorbance | Spectrum at Outlet from reactor Absorbance |
|---|---|---|---|
| 4640 | $D_{11}$ | 0.14633 | 0.15406 |
| 4385 | $D_{12}$ | 0.41282 | 0.40466 |
| 4305 | $D_{13}$ | 0.48511 | 0.50243 |
| 4210 | $D_{14}$ | 0.29911 | 0.29836 |
| 4135 | $D_{15}$ | 0.28855 | 0.28183 |

Using the spectrum of the feedstock, the value of the maleic anhydride number of the hydrogenated gasoline emerging from the reactor was determined by means of the following relation:

Maleic anhydride
number = $-325.05 - 1744.6.D_1 + 649.D_2 - 565.5.D_3 + 813.1.D_4 + 349.3.D_5 - 356.9.D_6 + 845.8.D_7 + 528.9.D_8 + 285.7.D_9 + 116.1.D_{10} + 124.3.6.D_{11} + 45.6.D_{12} - 333.9.D_{13} + 182.2.D_{14} - 1773.4.D_{15}$ The calculated value is 5.6 as against 7 by measurement.

EXAMPLE 5

Selective Hydrogenation

A similar exercise was carried out on the feedstock to the selective hydrogenation unit of Example 4.

The maleic anhydride number values were measured on the feedstock, using the feedstock spectrum and on the hydrogenated gasoline product using the feedstock spectrum according to the following relationship:

maleic anhydride
number = $-283.05 - 704.2.D_1 + 633.9.D_2 - 552.4.D_3 + 794.2.D_4 + 341.2.D_5 - 348.6.D_6 + 826.2.D_7 + 516.7.D_8 + 279.1.D_9 + 113.4.D_{10} + 1214.8.D_{11} + 35.25.D_{12} - 326.1.D_{13} + 178.1.D_{14} - 1732.3.D_{15}$ The following results are obtained:

| | Calculated | Measured |
|---|---|---|
| Maleic anhydride number on entry | 40 | 40.2 |
| Maleic anhydride number at exit | 8 | 7.8 |

This example shows that it is also possible to determine the value of the maleic anhydride number directly, using the product spectrum.

EXAMPLE 6

Hydrocracking

The feedstock was a distillate derived from crude petroleum from the Cameroons, KOLE.

The relative absorbance spectrum as a percentage of the total absorbance is as follows:
$D_4$ 18.43%
$D_5$ 13.06%
$D_6$ 13.98%
$D_7$ 12.12%
$D_8$ 11.87%

The KUOP factor of the feedstock was obtained from the following equation:

KUOP = $0.618\ D_4 + 0.36\ D_5 + 1.07\ D_6 - 0.248\ D_7 + 1.032\ D_8 - 28.5$

The KUOP factor as measured was 12.31 compared with a calculated value of 12.2.

EXAMPLE 7

Hydrocracking

A heavy aromatic distillate of KUOP factor 10.9 was used.

The relative absorbance spectrum of this feedstock was as follows:
$D_4$ 16.93%
$D_5$ 12.76%
$D_6$ 12.77%
$D_7$ 10.94%
$D_8$ 12.50%

The value for Conradson carbon residue may be determined by the following equation:

C % weight = $36.84 - 3.77.D_4 - 2.42.D_5 + 8.444\ D_6 - 6.473.D_7 + 2.023.D_8$

The value determined in this way is 4.5% by weight as against 5.5% by weight by experiment. This agreement is satisfactory, taking into account experimental accuracy.

Other correlations can be obtained for the nitrogen content and density of the feed.

EXAMPLE 8

Hydrocracking

The operating conditions used in this example were as follows:
Reactor - entry temperature 400° C.
Reactor - exit temperature 430° C.
Total pressure 155 bars
Hydrogen flow rate 1300 N m$^3$/m$^3$
Average temperature 423° C.
Catalyst: molybdenum cobalt on aluminium silicate.

The following correlations ccan be established for these operating conditions:

$$\text{Conversion \% by weight} = A + B \log_{10} \frac{(D_8)}{(D_4)} \quad (7)$$

$$\text{Conversion into gasoline \% by weight} = C \frac{D_8}{D_4} - D \quad (8)$$

A, B, C and D are constants linked to the operating conditions of the reactor.

For the conditions described above, the values of these constants are:
A = 123.12  B = 277.14  C = 35.893  D = 8.55

The unit is fed with a distillate, the characteristics of which are as follows:
Density: 0.952
KUOP factor: 11.5
nitrogen content 1735 ppm
Conradson carbon residue: 0.42% by weight
Saturated hydrocarbons: 37.20% by weight
Aromatic hydrocarbons: 61.30% by weight The absorption spectrum of the feedstock gives the following relative absorbance factors:
$D_8$ = 12.2
$D_4$ = 17.75

The application of equations (3) and (4) gives the following results by comparison with experimental figures:

|  | Calculated | Measured |
|---|---|---|
| Conversion into gasoline % by weight | 16.1 | 15 |
| Total conversion | 78 | 79.5 |

The reactor operating in the same conditions is fed with a different batch whose characteristics are as follows:
Density 0.920
KUOP factor 11.7
Nitrogen content 1300 ppm
Carbon residue 0.26% by weight
The relative absorbance factors are as follows:
$D_8 = 12.19$
$D_4 = 18.05$
The equations (7) and (8) give the following results:

|  | Calculated | Measured |
|---|---|---|
| Conversion into gasoline % by weight | 15.7 | 16.5 |
| Total conversion | 75.9 | 75 |

EXAMPLE 9

Catalytic Cracking

In this and the following Examples 10, 11 and 12 operating conditions were as follows:
Temperature at entry to riser: 250° C.
Temperature at exit from riser: 525° C.
Mass flow rate: 78 kg/h per kg
C/O: 6.6
Catalyst MAT activity ASTM-D 3907: 65
The feedstock had a KUOP factor of 11.95 and had the following absorption spectrum:
$F_1 = 4615$ cm$^{-1}$ $D_1 = 0.02395$
$F_2 = 4135$ $D_2 = 0.55726$
$F_3 = 4100$ $D_3 = 0.5193$
$F_4 = 4485$ $D_4 = 0.04015$ The gasoline yield had the following characteristics: ASTM distillation: initial boiling point 38° C., 90% distilled at 190° C., being 47.7% by weight.

The yield of residue following the ASTM distillation provided 10% distilled at 385° C., being 9% by weight.

The yields can be obtained from the feedstock spectrum by the following relationships, for the control conditions for the unit as given below:

$$\text{Yield of gasoline \% by weight} = 59.3 - 280 \frac{D_1}{D_2}$$

$$\text{Yield of residue \% by weight} = \frac{496.7}{\left(\frac{D_3}{D_4}\right)^{1.55}}$$

The results obtained are 47.27% for the yield of gasoline and 9.39% for the yield of residue, using these proportions.

EXAMPLE 10

Catalytic Cracking

A feedstock having a KUOP factor of 11.6 was used with the following spectrum measured under the same conditions as in Example 9:

| $F_1 = 4615$ cm$^{-1}$ | $D_1 = 0.3357$ |
|---|---|
| $F_2 = 4135$ | $D_2 = 0.52092$ |
| $F_3 = 4100$ | $D_3 = 0.48834$ |
| $F_4 = 4485$ | $D_4 = 0.04989$ |

The observed and calculated yields using the proportions as in Example 9 are:

|  | Observed | Calculated |
|---|---|---|
| Yield of gasoline % by weight | 40.6 | 41.25 |
| Yield of residue % by weight | 15 | 14.47 |

EXAMPLE 11

Catalytic Cracking

A feed of KUOP factor = 11.95 was used. This had the following absorption spectrum:

| $F_1 = 4670$ cm$^{-1}$ | $D_1 = 0.00977$ |
|---|---|
| $F_2 = 4485$ | $D_2 = 0.04015$ |
| $F_3 = 4100$ | $D_3 = 0.5193$ |
| $F_4 = 4060$ | $D_4 = 0.52665$ |

The following feed properties are obtained by the following relationships:
Density of the feed = $0.96497 + 4.1 D_1 - 0.1935 D_3$
Conradson carbon residue of the feed as % by weight = $-7.744 + 16.07 D_3 + 48.175 D_1$
Aniline point of feed in °C. = $70 - 500 (D_4/D_3) - 1.066$ The experimentally determined values and those calculated with the aid of the above correlations are as follows:

|  | Calculated | Found Experimentally |
|---|---|---|
| Density at 15° C. | 0.905 | 0.908 |
| % weight carbon residue | 1.07 | 1.10 |
| Aniline point °C. | 96 | 94.4 |

EXAMPLE 12

Catalytic Cracking

A feed of KUOP factor = 11.6 was used. The gasoline obtained by cracking had the following characteristics:
Distillation: initial boiling point 38° C., 90% distilled at 190° C.
Density at 15° C.: 0.749
Research octane number after addition of lead tetraethyl at 0.4 g/l: 92.4

The absorption spectrum for the feed is measured under the following conditions:

| Frequencies | Absorbance |
|---|---|
| $F_1 = 4670$ cm$^{-1}$ | $D_1 = 0.0155$ |
| $F_2 = 4485$ | $D_2 = 0.05079$ |
| $F_3 = 4100$ | $D_3 = 0.48692$ |
| $F_4 = 4060$ | $D_4 = 0.51066$ |

The characteristics of the gasoline produced are obtained from the spectrum of the feed from the following relationships:
Density of the gasoline = $0.7553 - 0.0355 \log_{10}(D_3/6.2 D_2)$ Research octane number after addition of lead tetraethyl at 0.4 g/l (RON 0.4) = 93.6 − 4.82 log$_{10}$ (D$_3$/6.2D$_2$)

The calculated values are d = 0.7486 and octane number 92.7 for experimentally determined values of d = 0.749 and octane number 92.4.

The process used therefore accurately predicts the experimental results obtained from the unit operated under the conditions established above.

EXAMPLE 13

Visbreaking

A feed was used consisting of a vacuum distillation residue obtained from a crude of Kuwait origin distilling above 565° C.

The product temperature on leaving the visbreaker was 481.4° C.

The following were determined from the NIR spectrum of the unit feed:
the visbreaking conversion,
the xylene equivalent of the visbreaking residue,
the gasoline yield.

The absorbances were determined at the following frequencies from the feed spectrum:

| Frequency (cm$^{-1}$) | Absorbance | |
|---|---|---|
| 4670 | D$_1$ | 0.00964 |
| 4640 | D$_2$ | 0.02301 |
| 4615 | D$_3$ | 0.02961 |
| 4585 | D$_4$ | 0.03566 |
| 4485 | D$_5$ | 0.05314 |
| 4385 | D$_6$ | 0.3485 |
| 4332 | D$_7$ | 0.6971 |
| 4305 | D$_8$ | 0.4710 |
| 4260 | D$_9$ | 0.5692 |
| 4210 | D$_{10}$ | 0.4019 |
| 4170 | D$_{11}$ | 0.3974 |
| 4135 | D$_{12}$ | 0.3546 |
| 4100 | D$_{13}$ | 0.3185 |
| 4060 | D$_{14}$ | 0.3381 |
| 4040 | D$_{15}$ | 0.2695 |
| 4405 | D$_{16}$ | 0.255 |

The xylene equivalent of the visbroken residue was determined by the following equation which links the absorbances and the reaction temperature T:

Xylene equivalent = −1553.9 + 1.849 T − 162
D$_1$ + 6824.8 (D$_3$) + 1027.9 (D$_5$) + 2480.9
(D$_6$) + 598.3 (D$_7$) − 1717.2 (D$_{10}$) + 7368.3
(D$_{11}$) − 8313 (D$_{14}$) − 573.4 (D$_{15}$) − 262.6 (D$_{16}$)

The experimentally determined xylene equivalent had a value of 79 as against a calculated value of 78.9.

The gasoline yield (C$_5$ cut − 185° C.) was obtained by the following equation:

Gasoline yield = 2.73 + 1166.2 (D$_5$) + 46.59
(D$_8$) − 253.03 (D$_{13}$)

The residue yield (cut point above 350° C.) was obtained by the following equation:

Residue yield = 20.46 + 2934.4 (D$_1$) − 3905.6
(D$_2$) + 173.39 (D$_7$)

The gasoline and residue yields determined by the equations above are respectively 6.07 and 79.75% weight.

A comparison with the values noted is shown below:

| | Calculated | Actual |
|---|---|---|
| Xylene equivalent | 79 | 78.9 |
| Gasoline yield % weight | 6.07 | 7.7 |
| Residue yield % weight | 79.75 | 78 |

EXAMPLE 14

Visbreaking

The reaction temperature which will give an xylene equivalent of 70 and obtain the corresponding gas oil yield was determined.

The temperature may be obtained by the following equation which links the xylene equivalent and the reaction temperature RT in °C.

RT = 840.4 + 0.54 xylene equivalent + 87.6
(D$_1$) − 3691.1 (D$_3$) − 555.9 (D$_5$) − 1341.75
(D$_6$) − 323.6 (D$_7$) + 928.7 (D$_{10}$) − 3985
(D$_{11}$) + 4495.9 (D$_{14}$) + 310.1 (D$_{15}$) + 142 (D$_{16}$)

The unit used operates under the same conditions as Example 13 and was fed with a vacuum distillation residue of Brent origin, the NIR spectrum of which has the following characteristics:

| Frequency (cm$^{-1}$) | Absorbance | |
|---|---|---|
| 4670 | D$_1$ | 0.01898 |
| 4640 | D$_2$ | 0.03318 |
| 4615 | D$_3$ | 0.03889 |
| 4585 | D$_4$ | 0.04543 |
| 4485 | D$_5$ | 0.06489 |
| 4385 | D$_6$ | 0.3789 |
| 4332 | D$_7$ | 0.7612 |
| 4305 | D$_8$ | 0.5216 |
| 4260 | D$_9$ | 0.6501 |
| 4210 | D$_{10}$ | 0.4613 |
| 4170 | D$_{11}$ | 0.4646 |
| 4135 | D$_{12}$ | 0.4265 |
| 4100 | D$_{13}$ | 0.389 |
| 4060 | D$_{14}$ | 0.4041 |
| 4040 | D$_{15}$ | 0.332 |
| 4405 | D$_{16}$ | 0.2688 |

The temperature determined by means of the above equation and the spectrum above was 480.4° C.

The gas oil yield was obtained by the following equation, linking the reaction temperature in °C. and the absorbances:

Gas oil yield, % weight = −290.45 + 0.34
(RT) + 626.5 (D$_6$) − 234.34 (D$_{14}$)

The gas oil yield obtained for the calculated temperature of 480.4° C. was 15.6% weight.

The actual and predicted results are given below:

| | Predicted | Actual |
|---|---|---|
| Xylene equivalent | 70 | 60 |
| RT °C. | 480.4 | 480 |
| Gas oil yield, % weight | 15.6 | 14.8 |

EXAMPLE 15

Visbreaking

The conversion limits of the Kuwait and Brent feedstocks of Examples 13 and 14 were determined from the spectra given in Examples 13 and 14 under the operating conditions of Example 13.

The conversion limit value was determined by the following equation:

$$CL = -53.05 + 917.83\ (D_5) + 1903.94\ (D_{12}) - 2090.1\ (D_{13}) + 55.86\ (D_{16})$$

The actual and calculated values were as follows:

|        | Calculated | Actual |
|--------|------------|--------|
| Brent  | 20.5       | 21.1   |
| Kuwait | 19.4       | 19.9   |

EXAMPLE 16

Distillation

In this Example and the following Examples 17–23, the experimental distillation procedure was carried out on a distillation column having an efficiency of 14 theoretical plates.

The NIR spectra of three crude oils was determined. The values of the absorbances for these three crude oils are as follows at the frequencies used, the base line being taken as 4870 cm$^{-1}$:

|  |  | Absorbances $D_1$ | | |
|---|---|---|---|---|
| Crude Oil | Iranian Heavy | Zakum | Djeno | Mixture 50-35-15 |
| Frequencies $F_i$ cm$^{-1}$ | | | | |
| $F_3$ 4615 | 0.02736 | 0.0248 | 0.01758 | 0.0251 |
| $F_4$ 4585 | 0.02671 | 0.02562 | 0.01895 | 0.0255 |
| $F_5$ 4485 | 0.03811 | 0.03981 | 0.02172 | 0.0379 |
| $F_7$ 4332 | 0.93621 | 0.96899 | 0.94434 | 0.9494 |
| $F_9$ 4260 | 0.77561 | 0.79598 | 0.80701 | 0.7876 |
| $F_{11}$ 4170 | 0.55478 | 0.56599 | 0.57862 | 0.5622 |
| $F_{13}$ 4100 | 0.49855 | 0.50971 | 0.51222 | 0.5050 |
| $F_{14}$ 4060 | 0.53475 | 0.54304 | 0.52624 | 0.5361 |
| $F_{15}$ 4040 | 0.41833 | 0.42156 | 0.41788 | 0.4196 |

A homogeneous mixture of the three crude oils was produced in the following proportions: Iranian Heavy: 50% by weight - Zakum: 35% by weight - Djeno: 15% by weight.

The last column in the above table indicates the absorbances obtained by analysis of the mixture.

By a least square method the nine equations are solved in relation to the three unknowns (% by weight of each of the crude oils in the mixture).

The values thus calculated are as follows, in % by weight: Iranian Heavy: 51.4% - Zakum: 34.2% - Djeno: 14.4%

The accuracy, in relation to the control mixture, is therefore satisfactory, the differences observed being acceptable and due to the repeatability of the absorbance measurements.

This method enables the composition of a mixture of known crude oils to be obtained in real time.

It is therefore possible, if the distillation unit is supplied from tanks containing different crude oils, to know, in real time, the composition of the mixture of crude oils which is supplied to the distillation unit.

This method may be applied to measuring the supplies of mixed crude oils.

EXAMPLE 17

Distillation

A Djeno crude oil was used and the absorbances $D_i$ were measured for 12 frequencies $F_i$. The results are summarised below:

| $F_2$ | 4640 cm$^{-1}$ | $D_2$ = 0.01364 |
|-------|----------------|-----------------|
| $F_3$ | 4615 | $D_3$ = 0.01758 |
| $F_4$ | 4584 | $D_4$ = 0.01895 |
| $F_5$ | 4485 | $D_5$ = 0.03172 |
| $F_6$ | 4385 | $D_6$ = 0.45629 |
| $F_7$ | 4332 | $D_7$ = 0.94434 |
| $F_8$ | 4305 | $D_8$ = 0.63842 |
| $F_9$ | 4260 | $D_9$ = 0.80701 |
| $F_{11}$ | 4170 | $D_{11}$ = 0.57862 |
| $F_{13}$ | 4100 | $D_{13}$ = 0.51222 |
| $F_{14}$ | 4060 | $D_{14}$ = 0.52624 |
| $F_{15}$ | 4040 | $D_{15}$ = 0.41788 |

The yields of the defined fractions previously obtained by multivariate regression are expressed as a function of the absorbances $D_i$ of the different frequencies by the following expressions:

$$\text{Residue output} = 359.88 - 1385.51\ D_2 - 441.15\ D_6 - 291.84\ D_7 + 225.1\ D_8 + 128.33\ D_{15}$$

$$\text{Light distillate output} = -113.6 + 541.26\ D_2 - 108.75\ D_6 + 122.71\ D_7 - 55.49\ D_8 - 31.64\ D_{15}$$

$$\text{Gas oil output} = -54.03 + 373.77\ D_2 + 199.13\ D_6 + 67.77\ D_7 - 101.61\ D_8 - 57.92\ D_{15}$$

The calculation carried out on the basis of the above formulae and of the absorbances gives the following results, compared with the experimental values observed for the Djeno crude oil examined here:

|                               | Calculated | Observed |
|-------------------------------|------------|----------|
| Yield of residue, % by weight | 61.4       | 63       |
| Light distillate              | 10.6       | 9.1      |
| Gas oil                       | 16.8       | 16.2     |

If this type of regression method is extended to the entire distillation range, it is then possible to calculate the distillation curve and the mean distillation temperature of the feed in real time.

This method is also applicable to mixtures and feedstocks of variable compositions.

In a computer-assisted process in a distillation unit, the NIR spectrum of the feedstock entering the unit is thus taken in real time and treated as an information vector which characterises the distillation properties of the feedstock in the distillation process on a continuous basis. The amount of detail in the near infra red spectrum and the experimental accuracy which may be obtained as required from the accumulation of spectral data, using fast Fourier transformation, ensures that this information is reliable and relevant to distillation.

In the following examples it is demonstrated that for a fixed set of conditions in the unit, the variations of the quantity of the products formed may be correlated, by means of a numerical treatment, with variations in the NIR spectrum of the feedstock.

EXAMPLE 18

Distillation

The Conradson carbon residue according to Standard T60-116) of a crude petroleum of Mexican ISTHMUS origin was 4.1% by weight.

The absorbances of a test sample of this crude petroleum were measured for 3 frequencies, and had the following values:

| $F_2$ | 4640 cm$^{-1}$ | $D_2 = 0.0186$ |
|---|---|---|
| $F_7$ | 4332 | $D_7 = 0.9435$ |
| $F_8$ | 4305 | $D_8 = 0.6374$ |

The value for the carbon residue was calculated from the following equation:

$$C = 84.306 - 64.1794\ D_7 - 252.437\ D_2 - 22.432\ D_8/D_7$$

In the case of the crude petroleum, the figure of 3.9% by weight was obtained, which was satisfactory, taking into account the accuracy of the test.

EXAMPLE 19

Distillation

The asphaltene content of a crude petroleum of Suez Blend origin, measured by the AFNOR T60 - 115 method was 1.5% by weight.

The NIR spectrum of this crude was determined at the following frequencies and gave the following absorbances:

| $F_2$ | 4640 cm$^{-1}$ | $D_2 = 0.01868$ |
|---|---|---|
| $F_7$ | 4332 | $D_7 = 0.93972$ |
| $F_8$ | 4305 | $D_8 = 0.6358$ |
| $F_2$ | 4640 cm$^{-1}$ | $D_2 = 0.0210$ |
| $F_7$ | 4332 | $D_7 = 0.9362$ |
| $F_8$ | 4305 | $D_8 = 0.6427$ |

The asphaltene content was obtained by the following equation correlating the absorbances:

$$\text{Asphaltenes (\% by weight)} = 22.31\ (3.758 - 2.861\ D_7 - 11.253\ D_2 - D_8/D_7)^{1.5} - 0.465$$

The calculated value was 1.3% by weight which was satisfactory.

EXAMPLE 20

Distillation

A gas oil fraction was used which was taken from a Iranian Heavy crude petroleum. The cetane number of this fraction was 49.6 (Standard MD7 - 035).

The NIR spectrum was obtained for the crude petroleum. Absorbances $D_i$ were measured at the following frequencies:

The absorbance values were used in the following equation in order to calculate the cetane number of the gas oil from the NIR spectrum of the crude:

$$\text{Cetane number} = 155.529 - 12.053\ D_7 - 47.408\ D_2 - 135.217\ D_8/D_7$$

The value obtained was 50.4.

Thus, the above equation enables the cetane number of a gas oil to be determined as a function of the NIR spectrum of the feedstock.

EXAMPLE 21

Distillation

The aniline point of a gas oil fraction from a light crude petroleum of Lokele, Cameroons origin, was determined (Standard ASTM-D611). This was 52° C.

The values for the absorbances measured at the following 4 frequencies of the NIR spectrum of this crude petroleum were:

| $F_6$ | 4385 cm$^{-1}$ | $D_6 = 0.5181$ |
|---|---|---|
| $F_7$ | 4332 | $D_7 = 0.8268$ |
| $F_8$ | 4305 | $D_8 = 0.6786$ |
| $F_{15}$ | 4040 | $D_{15} = 0.4293$ |

The following equation enabled the aniline point to be calculated from the absorbances of the crude:

$$\text{Aniline point of the gas oil produced} = 27.1 + 53.57\ D_7 + 113.8\ D_{15} + 199.6\ D_8 - 391.2\ D_6$$

The value thus calculated was 53° C.

EXAMPLE 22

Distillation

The cloud point of a gas oil fraction taken from an Egyptian Belayim Crude was −10° C. (Standard T60 - 105).

The values for the absorbances measured at the following four frequencies of the NIR spectrum of a sample of this crude petroleum were:

| $F_5$ | 4485 cm$^{-1}$ | $D_5 = 0.0335$ |
|---|---|---|
| $F_6$ | 4385 | $D_6 = 0.45821$ |
| $F_{13}$ | 4100 | $D_{13} = 0.49486$ |
| $F_{15}$ | 4040 | $D_{15} = 0.41039$ |

EXAMPLE 23

The viscosity at 60° C. of the 369°–509° C. fraction of a Congolese Djeno crude petroleum was 27.2 cSt.

The values for the absorbances measured at four frequencies of the NIR spectrum of a sample of this crude petroleum were:

| $F_2$ | 4640 cm$^{-1}$ | $D_2 = 0.01364$ |
|---|---|---|
| $F_7$ | 4332 | $D_7 = 0.94434$ |
| $F_8$ | 4305 | $D_8 = 0.63842$ |
| $F_{14}$ | 4060 | $D_{14} = 0.52624$ |

The value calculated by introducing the measured absorbances in the following equation was:

$$\log_{10} \text{viscosity at 60° C.} = 1.4468 - 5.662\ D_7 + 0.874\ D_{14} = 29.980\ D_2 + 8.310\ D_8 = 28.5\ \text{cSt}$$

The equation enabled the viscosity of the residue to be calculated from the NIR spectrum of the feedstock.

We claim:

1. The method for determining at least one of a property of a product and a yield of a product from a process selected from the group consisting of a hydrocarbon conversion process and a hydrocarbon separation process, comprising the following steps:

(a) determining with an infrared spectrometer an absorbance of a feedstock to the process at a certain number of frequencies in the spectral range 16667 to 3840 cm$^{-1}$, starting from a defined base line, and (b) determining at least one of (i) the property by applying a correlation between the property of the product and the absorbance values of the feedstock and (ii) the yield by applying a correlation between the yield of the product and the absorbance values of the feedstock wherein the correlation is determined experimentally by multivariate regression and is dependent upon the spectrometer used, the property or yield to be determined, and the frequencies used.

2. The method according to claim 1 wherein the frequencies are in the spectral range 12500 to 3840 cm$^{-1}$.

3. The method according to claim 2 wherein the frequencies are in the spectral range 4760 to 4000 cm$^{-1}$.

4. The method according to claim 1 wherein the frequencies used are selected from the following:
4670 cm$^{-1}$
4640 cm$^{-1}$
4615 cm$^{-1}$
4585 cm$^{-1}$
4485 cm$^{-1}$
4405 cm$^{-1}$
4390 cm$^{-1}$
4385 cm$^{-1}$
4332 cm$^{-1}$
4305 cm$^{-1}$
4260 cm$^{-1}$
4210 cm$^{-1}$
4170 cm$^{-1}$
4135 cm$^{-1}$
4100 cm$^{-1}$
4070 cm$^{-1}$
4060 cm$^{-1}$, and
4040 cm$^{-1}$.

5. The method according to claim 1 wherein the base line is taken as 4780 cm$^{-1}$.

6. The method according to claim 1 wherein the spectrometer is linked to a signal processing device to permit numerical treatment of the spectral range.

7. The method according to claim 6 wherein the treatment is by Fourier transformation.

8. The method according to claim 1 wherein the method is on-line and in real time.

9. The method according to claim 1 wherein the correlation contains linear terms, quadratic terms and homographic terms.

10. The method according to claim 1 wherein the process is a hydrocarbon conversion process which is a catalytic reforming process and the properties are selected from the following: yields of gasoline (C$_5$+), hydrogen and gas, octane numbers (clear or leaded), vapor pressure and density.

11. The method according to claim 1 wherein the process is a hydrocarbon conversion process which is a catalytic reforming process and wherein the method comprises the further steps of:

(c) carrying out differential spectrum measurements on the feedstock and the product in a range and at frequencies which are the same for the feedstock and the product, (d) applying a correlation between the differential spectrum and an octane number gain determined for the product, the correlation being determined experiment by multivariate regression analysis, (e) determining an octane number and octane number gain for the product and comparing a sum of the octane number and octane number gain with a desired objective, and (f) modifying at least one operating condition of the catalytic reforming process until the determined octane number gain is in agreement with a desired octane number gain.

12. The method according to claim 10 wherein the frequencies used are selected from the following:
4670 cm$^{-1}$
4485 cm$^{-1}$
4332 cm$^{-1}$
4305 cm$^{-1}$
4210 cm$^{-1}$
4100 cm$^{-1}$
4060 cm$^{-1}$, and
4040 cm$^{-1}$.

13. The method according to claim 1 wherein the process is a hydrocarbon conversion process which is a selective hydrogenation process and the property is a maleic anhydride number of the product.

14. The method according to claim 1 wherein the process is a hydrocarbon conversion process which is a catalytic hydrocracking process and the properties are selected from the following: total conversion of the feedstock to product and conversion of the feedstock to gasoline.

15. The method according to claim 14 wherein the frequencies used are selected from the following:
4585 cm$^{-1}$
4390 cm$^{-1}$
4332 cm$^{-1}$
4260 cm$^{-1}$
4210 cm$^{-1}$
4170 cm$^{-1}$
4100 cm$^{-1}$, and
4070 cm$^{-1}$.

16. The method according to claim 1 wherein the process is a hydrocarbon conversion process which is a catalytic cracking process and the properties are selected from the following:

(i) conversion of the feedstock to gasoline and yield of residue in the product, and (ii) density, research octane number (RON) and motor octane number (MON) of clear and leaded gasoline from the catalytic cracking process.

17. The method according to claim 16 wherein the frequencies used are selected from the following:
4670 cm$^{-1}$
4615 cm$^{-1}$
4485 cm$^{-1}$
4135 cm$^{-1}$
4100 cm$^{-1}$, and
4060 cm$^{-1}$.

18. The method according to claim 1 wherein the process is a hydrocarbon conversion process which is a visbreaking process and the properties are selected from the following: yield of a gas oil product, viscosity, specific gravity and xylene equivalent of residue, and conversion limit.

19. The method according to claim 1 wherein the process is a hydrocarbon separation process which is a distillation process and the properties are selected from the following:

(i) a quantitative composition of a mixture of crude oils constituting the feedstock when the product is known to be a blend of crude oils, (ii) yields of products obtained, (iii) densities and viscosities of the products, (iv) cetane number, aniline point, cloud point and KUOP characterisation factor of a gas oil product, and (v) n-paraffinic, isoparaffinic, cycloparaffinic and aromatic content of a gasoline product and a research octane number (RON) and motor octane number (MON) of clear and leaded gasoline.

20. The method according to claim 1 wherein a value of at least one of a property or yield of a product is determined by an NIR spectrum of the feedstock, and wherein the process is computer controlled by a feedback control system which will alter process conditions in response to variations in that value from a desired value.

21. An apparatus for carrying out a method for determining at least one of a property of a product and a yield of a product from a process selected from the group consisting of a hydrocarbon conversion process and a hydrocarbon separation process, wherein the method comprises the following steps:

(a) determining with an infrared spectrometer an absorbance of a feedstock to the process at a certain number of frequencies in the spectral range 16667 to 3840 $cm^{-1}$, starting from a defined base line, and (b) determining at least one of (i) the property by applying a correlation between the property of the product and the absorbance values of the feedstock, and (ii) the yield by applying a correlation between the yield of the product and the absorbance values of the feedstock, wherein the correlation is determined experimentally by multivariate regression and dependent upon the spectrometer used, the property or yield to be determined, and the frequencies used;

said apparatus comprises an infrared spectrometer and a computer wherein the computer is programmed to receive and utilize the absorbance from the infrared spectrometer to determine the at least one of the property and yield continuously and in real time.

22. The apparatus according to claim 21 wherein a value of at least one of a property or yield of a product is determined by an NIR spectrum of the feedstock, and wherein the process is computer controlled by a feedback control system which will alter process conditions in response to variations in that value from a desired value.

* * * * *

UNITED STATES PATENT AND TRADEMARK OFFICE
CERTIFICATE OF CORRECTION

PATENT NO. : 5,452,232
DATED : September 19, 1995
INVENTOR(S) : ALAIN ESPINOSA, DIDIER C. LAMBERT, ANDRE MARTENS and GILBERT VENTRON It is certified that error appears in the above-indentified patent and that said Letters Patent is hereby corrected as shown below:

Col. 9, l. 34, Example 5, change "704.2" to --1704.2--

Col. 18, line 61, Example 23, after "D14" change the equal sign (=) to a minus sign (-)

Column 18, line 1, change "The" to --A--

Column 20, line 2, correct the spelling of the word "experimentally".

Signed and Sealed this

Twentieth Day of February, 1996

Attest:

BRUCE LEHMAN

Attesting Officer

Commissioner of Patents and Trademarks